(12) United States Patent
Peterson et al.

(10) Patent No.: US 12,146,507 B2
(45) Date of Patent: Nov. 19, 2024

(54) AIR WARMER

(71) Applicant: Smiths Medical ASD, Inc., Plymouth, MN (US)

(72) Inventors: Benjamin James Peterson, Apple Valley, MN (US); Ahmed Reda, Brooklyn Center, MN (US); Jonathan Harold Sanborn, St Louis Park, MN (US); Michael A. Treppa, Blaine, MN (US)

(73) Assignee: ICU Medical, Inc., San Clemente, CA (US)

( * ) Notice: Subject to any disclaimer, the term of this patent is extended or adjusted under 35 U.S.C. 154(b) by 674 days.

(21) Appl. No.: 15/491,004

(22) Filed: Apr. 19, 2017

(65) Prior Publication Data

US 2017/0306984 A1    Oct. 26, 2017

Related U.S. Application Data

(60) Provisional application No. 62/325,502, filed on Apr. 21, 2016.

(51) Int. Cl.
*F04D 29/66* (2006.01)
*A61F 7/00* (2006.01)
(Continued)

(52) U.S. Cl.
CPC .......... *F04D 29/664* (2013.01); *A61F 7/0085* (2013.01); *A61F 7/0097* (2013.01);
(Continued)

(58) Field of Classification Search
CPC ...... F04D 25/084; F04D 25/08; F04D 29/664; A61F 2007/006; A61F 2007/0095;
(Continued)

(56) References Cited

U.S. PATENT DOCUMENTS 2,297,046 A * 9/1942 Bourne .................. F01N 1/006
    181/250
3,613,830 A * 10/1971 Hubbell, III .......... B21D 53/88
    181/266
(Continued)

FOREIGN PATENT DOCUMENTS

CN    2073503 U    3/1991
CN    2231387 Y    7/1996
(Continued)

OTHER PUBLICATIONS

Raw Machine Translation of JP 2001193979A, Hikosaka Masuo, "Room Air Recirculation Apparatus" Jul. 17, 2001.*
(Continued)

*Primary Examiner* — Charles G Freay
*Assistant Examiner* — Lilya Pekarskaya
(74) *Attorney, Agent, or Firm* — Louis Woo

(57) ABSTRACT

An air blower has an inlet muffler and an outlet muffler to reduce the noise of the air blower during operation. Each of the mufflers may have two sections. One section is configured to attenuate high frequency noise and the other section is configured to attenuate lower frequency noise. A tubular internal wall in each of the mufflers defines the through passage for each of the mufflers. A noise absorbent material may be fitted about the tubular wall within each muffler. A plurality of holes are formed along the tubular wall of each through passage to expose the through passage to the noise absorbent material. A heater plenum may be interposed between the blower plenum and the outlet muffler to heat the air from the blower plenum. A filter at the input muffler filters the air sucked into the air blower.

20 Claims, 14 Drawing Sheets

(51) Int. Cl.
*F04D 25/08* (2006.01)
*F01N 1/04* (2006.01)
*F01N 1/24* (2006.01)
*F02M 35/12* (2006.01)

(52) U.S. Cl.
CPC ........... *F04D 25/08* (2013.01); *F04D 25/084* (2013.01); *F04D 29/665* (2013.01); *A61F 2007/006* (2013.01); *A61F 2007/0091* (2013.01); *A61F 2007/0093* (2013.01); *A61F 2007/0095* (2013.01); *A61F 2007/0096* (2013.01); *F01N 1/04* (2013.01); *F01N 1/24* (2013.01); *F02M 35/1233* (2013.01); *F02M 35/1272* (2013.01)

(58) Field of Classification Search
CPC ........ A61F 2007/0093; F02M 35/1233; F02M 35/1266; F02M 35/1272; F01N 1/04; F01N 1/24
USPC ................ 415/203, 205, 206, 119; 417/312; 181/403, 250
See application file for complete search history.

(56) References Cited

U.S. PATENT DOCUMENTS

| | | | | |
|---|---|---|---|---|
| 4,267,899 A | * | 5/1981 | Wagner | F01N 1/003 181/272 |
| 4,416,350 A | * | 11/1983 | Hayashi | F01N 1/02 181/265 |
| 4,693,339 A | * | 9/1987 | Beale | F02M 35/1233 181/229 |
| 4,905,789 A | * | 3/1990 | Francis | A61M 16/0057 181/224 |
| 5,530,214 A | * | 6/1996 | Morehead | F02M 35/12 181/229 |
| 5,567,127 A | | 10/1996 | Wentz | |
| 5,983,888 A | * | 11/1999 | Anselmino | F04D 29/664 126/299 D |
| 6,143,020 A | * | 11/2000 | Shigezawa | A61F 7/0085 607/104 |
| 7,770,694 B2 | * | 8/2010 | Baars | F04B 39/0066 181/229 |
| 8,702,379 B2 | * | 4/2014 | Frater | A61M 16/0057 128/204.18 |
| 2001/0005225 A1 | | 6/2001 | Clark et al. | |
| 2008/0286092 A1 | * | 11/2008 | Pierre | F04D 29/663 415/119 |
| 2015/0176860 A1 | * | 6/2015 | Hattan | F24H 3/0405 392/368 |
| 2017/0122329 A1 | * | 5/2017 | Son | F04D 29/444 |

FOREIGN PATENT DOCUMENTS

| | | |
|---|---|---|
| CN | 2561976 Y | 7/2003 |
| CN | 202228435 U | 5/2012 |
| CN | 202659591 U | 1/2013 |
| CN | 204512005 U | 7/2015 |
| JP | 2001193979 A * | 7/2001 |

OTHER PUBLICATIONS

PCT International Search Report re corresponding PCT application No. PCT/US2017/028479, ISA/KR, Jul. 20, 2017.
Chinese patent office action for CN application No. 201780024407.X dated Apr. 3, 2020.
EP Rule 71(3) Communication for corresponding EP application No. 17786597.9 dated Oct. 23, 2023.
Pages 1-1A of amended text of EP application No. 17786597.9 accompanying EP Rule 71(3) Communication.

* cited by examiner

AIR WARMER

FIELD OF THE INVENTION

The present invention relates to air warmers and particularly an air convective warmer that is adapted to provide an optimum throughput of temperature regulated air to inflate a convective blanket while operating at a reduced noise level.

BACKGROUND OF THE INVENTION

An air convective warmer is used to inflate a convective blanket that provides a constant stream of heated air to warm a patient to regulate the body temperature of the patient. There are myriad air convective warmers being sold in the market, including an air convective warmer sold by the assignee under the trade name EQUATOR®. Most of these air convective warmers tend to produce a high level of noise. The noise is mostly due to the air turbulence that results from the rotation of the fan or impeller in the air plenum of the warmer needed to suck air into the plenum from the environment and to propel a stream of pressurized air, heated or otherwise, to inflate the convective blanket.

Attempts have been made to reduce the noise of air convective warmers. One such attempt, as disclosed in U.S. Pat. No. 6,126,393 and its related U.S. Pat. No. 6,254,337, relies on the relative orientation of the air inlet and air outlet of the warmer. Another attempt, as disclosed in U.S. Pat. No. 5,733,320, uses noise cancellation components. Yet other attempts to reduce the noise level of an air convective warmer are disclosed in U.S. Pat. Nos. 7,037,068 and 8,720,220, both assigned to the assignee of the instant application. The '068 patent discloses forming indentations at the interior surface of the plenum chamber, and the '220 patent discloses the use of a noise reduction air filter.

SUMMARY OF THE PRESENT INVENTION

The inventive air convective warmer has an air blower that has a motor assembly that includes a fan or impeller positioned in an air plenum. The impeller is connected to a shaft that extends from a motor. The plenum has an air inlet and an air outlet, and a cavity so that air can circulate within the plenum. Positioned to the inlet side of the plenum is a first noise reduction structure, or an inlet muffler, that has two cylindrical sections and a through passage longitudinally extending along the sections to effect a fluid conduit connecting the inlet and an outlet of the inlet muffler. One of the cylindrical sections is designed to attenuate high frequency noise while the other of the sections is designed to attenuate low frequency noise. For the exemplar inlet muffler, the section that attenuates the lower frequency noise has a larger diameter than the section that reduces the high frequency noise. Thus, the inlet muffler for the exemplar air blower has a telescopic shape, with the wider section (in terms of its diameter) being positioned adjacent to the inlet side of the plenum, and the outlet of the inlet muffler in alignment with the inlet of the plenum to establish a fluid communication path between the inlet muffler and the air plenum of the motor assembly.

A filter is fittingly coupled to the inlet side of the air inlet muffler to filter the air sucked into the convective warmer from the environment.

The outlet of the air plenum is in fluid communication with an inlet of a heater plenum. The heater plenum may be configured to have an elbow shape to reduce the turbulence of air flowing through it. A plurality of heating elements are mounted in the heater plenum to heat the air flow that enters it from the air plenum.

The outlet of the heater plenum is in fluid communication with an inlet of an outlet noise reduction structure, or an outlet muffler, that also has an outlet. The outlet muffler has two sections. One of the sections is designed to reduce high frequency noise and the other of the sections is designed to attenuate low frequency noise. A central through passage extends longitudinally along the two sections to effect a fluid conduit connecting the inlet and outlet of the outlet muffler. The heated air from the heater plenum flows through the fluid conduit of the outlet muffler. At the outlet of the outlet muffler there is an extension adapted to be connected to a machine end of an air hose which other end is connected to an input port of a convective blanket.

When the air convective blower is in operation, air from the environment is sucked into the air plenum and a stream of pressurized airflow having a certain velocity is output from the air plenum. The air output from the air plenum is routed to the heater plenum where it is heated. The heated air then passes through the outlet muffler to inflate the convective blanket. With an inlet muffler and an outlet muffler sandwiching the air plenum of the motor assembly, the noise resulting from the operation of the air convective blower when the impeller is in motion is substantially reduced. Lab tests show that the inventive convective air warmer has a noise level that is below most, if not all, of the known convective air warmers.

Each section of each of the inlet and outlet mufflers may be fitted with a noise absorbent material such as a sound absorbing foam. Alternatively, one of the sections, for example the lower frequency noise attenuation section, is fitted with the noise absorbent material while the high frequency noise attenuation section is configured as a Helmholtz chamber. The inlet muffler may be a one piece integral component having a telescopic shape with a large cylindrical section and a small cylindrical section. The outlet muffler may also be a one piece integral component but with an oblong large section and a small cylindrical section. The various components of the inventive air convective warmer may be encased in a housing that has displays, inputs and other interfacing means to enable a user or clinician to operate the air convective warmer.

The present invention is therefore directed to an air blower comprising: a plenum wherein an impeller is movably positioned, the plenum having an inlet and an outlet; a motor working cooperatively with the impeller for rotating the impeller; an inlet noise reduction structure positioned relative to the plenum including a housing having at least one wide section and one narrow section encircling an inlet through passage, the one wide section positioned adjacent to the plenum so that the inlet through passage is in fluid communication with the inlet of the plenum to establish a fluid communication path between the inlet through passage and the plenum, a noise absorbent material fitted to at least one of the wide and narrow sections to surround a corresponding portion of the inlet through passage; wherein when the motor is activated, the impeller is rotated to draw air into the plenum from the inlet through passage and to output a stream of air flow through the outlet of the plenum; and wherein a portion of the noise resulting from the movement of air in the plenum is reduced by the inlet noise reduction structure.

The invention is also directed to an air blower that comprises a motor assembly including a motor, a plenum and an impeller workingly coupled to the motor movably positioned inside the plenum; the plenum having an inlet and an outlet; an inlet muffler coupled to the plenum, the inlet muffler including a housing having an outer wall and an inlet through passage connecting an inlet and an outlet of the inlet muffler, the outlet of the inlet through passage in fluid communication with the inlet of the plenum, a sound absorbent material fitted between the outer wall of the housing and an inner circumferential wall of the housing that defines the inlet through passage; an outlet muffler including a housing having an outer wall and an outlet through passage connecting an inlet and an outlet of the outlet muffler, the outlet muffler positioned relative to the plenum so that the outlet through passage is in fluid communication with the outlet of the plenum, a sound absorbent material fitted between the outer wall and an inner circumferential wall of the housing that defines the outlet through passage; and an air filter coupled to the inlet muffler so that air sucked into the plenum is filtered by the air filter; wherein when the motor assembly is in operation, the air sucked into the inlet through passage is passed to the plenum and output therefrom to the outlet through passage as a stream of air flow; and wherein sound resulting at least from air turbulence due to movement of the air in the plenum during operation of the motor assembly is reduced by both the inlet and outlet mufflers.

The instant invention is moreover directed to an air blower that comprises: a motor assembly including a motor, a plenum and an impeller workingly coupled to the motor movably positioned inside the plenum, the plenum having an inlet and an outlet; an inlet muffler including an inlet through passage having an outlet in fluid communication with the inlet of the plenum, a low frequency noise attenuation section and a high frequency attenuation section; an outlet muffler including an outlet through passage having an inlet in fluid communication with the outlet of the plenum, a low frequency noise attenuation section and a high frequency attenuation section; wherein when the motor is activated to rotate the impeller in the plenum, air is sucked into the inlet muffler and a stream of air flow is output from the outlet of the outlet muffler; and wherein the inlet and outlet mufflers act to reduce noise resulting from operation of the air blower.

BRIEF DESCRIPTION OF THE FIGURES

The present invention will become apparent and the invention itself will be best understood with reference to the following description of the invention taken in conjunction with the accompanying drawings, wherein.

DETAILED DESCRIPTION OF THE INVENTION

Figure 1:
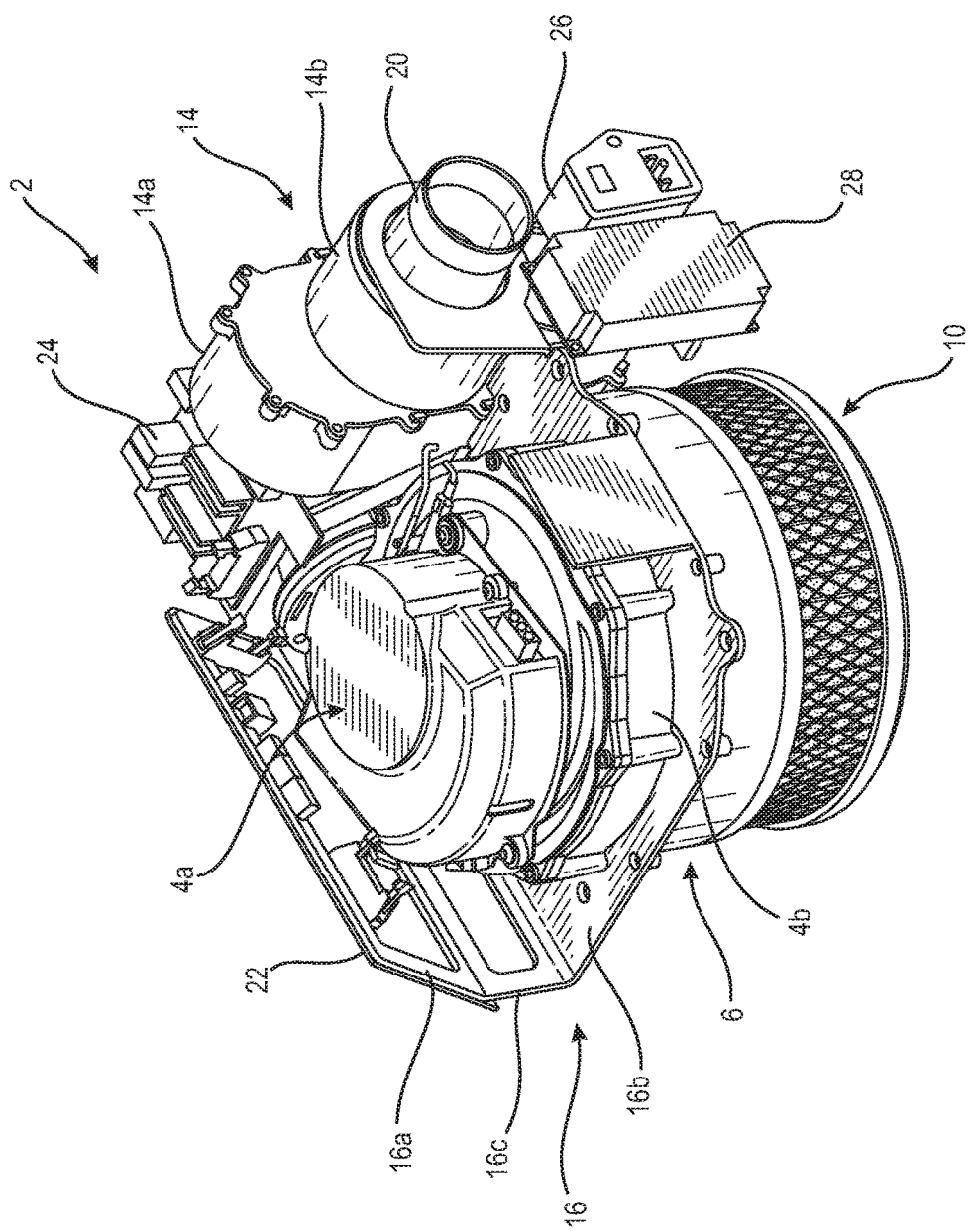
FIG. 1 is a perspective view of an embodiment of the inventive air convective warmer.

With reference to FIGS. 1-6, an embodiment of the inventive air convective warmer 2 is shown to have a motor assembly 4, a first noise reduction structure referenced hereinbelow as an inlet muffler 6, a filter 10, a heater plenum 12 and an outlet noise reduction structure referred to hereinbelow as an outlet muffler 14. All of the major components of the embodiment air convective warmer 2 are either attached, or positioned relative, to a structural frame 16.

Figure 3:
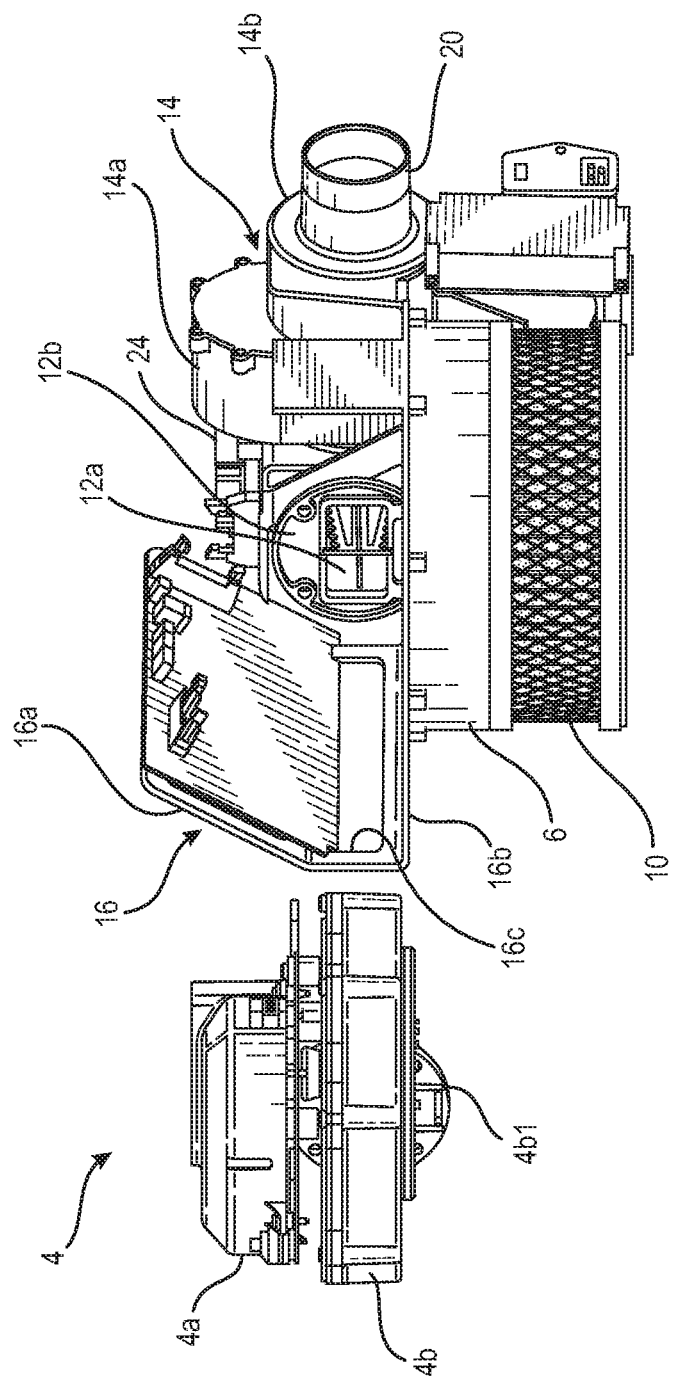
FIG. 3 is another view of the air convective warmer with the motor assembly removed from the frame to show the inlet opening to the heater plenum.
Figure 6:
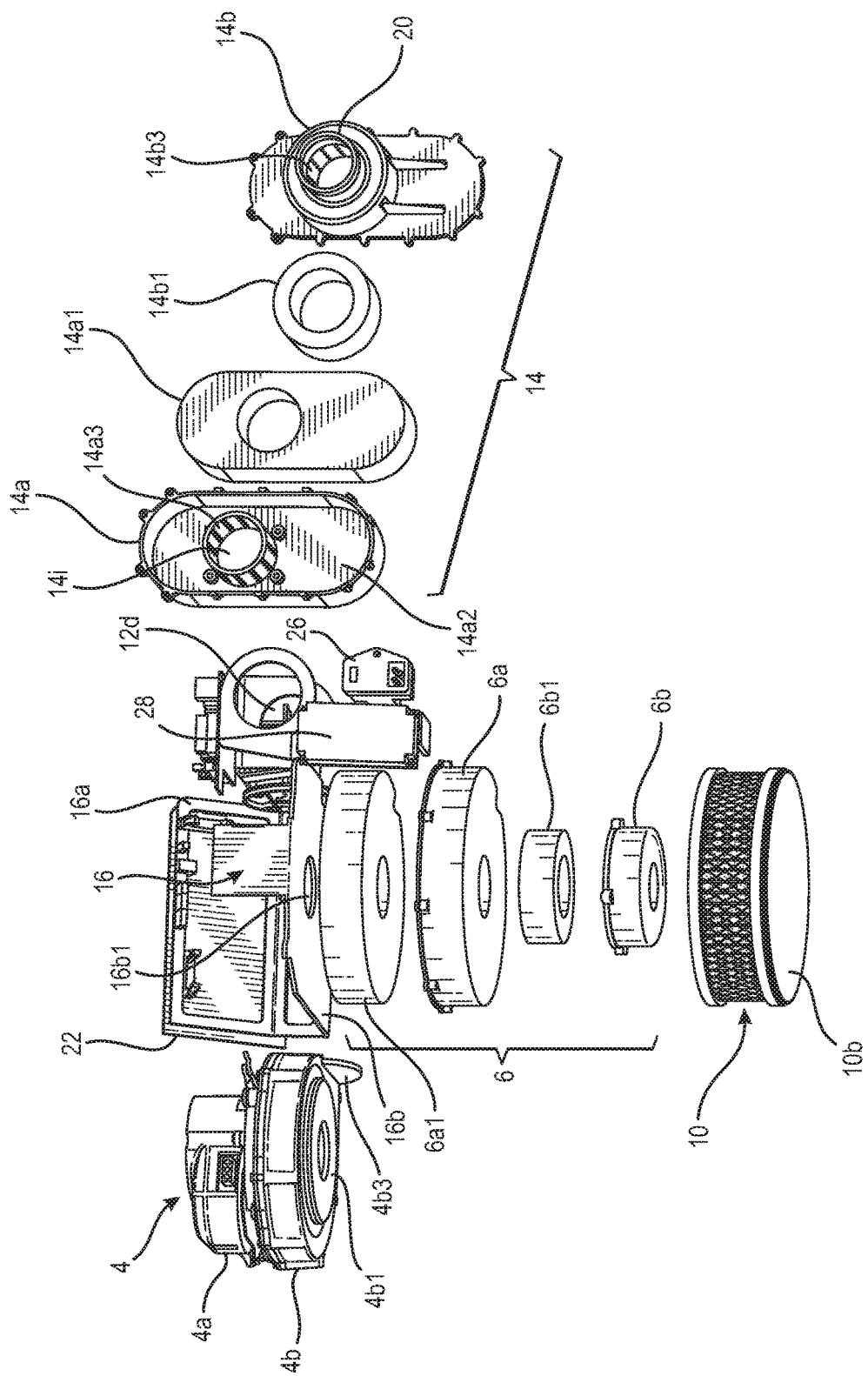
FIG. 6 is a disassembled illustration of the inventive air convective warmer showing its various components.
Figure 7:
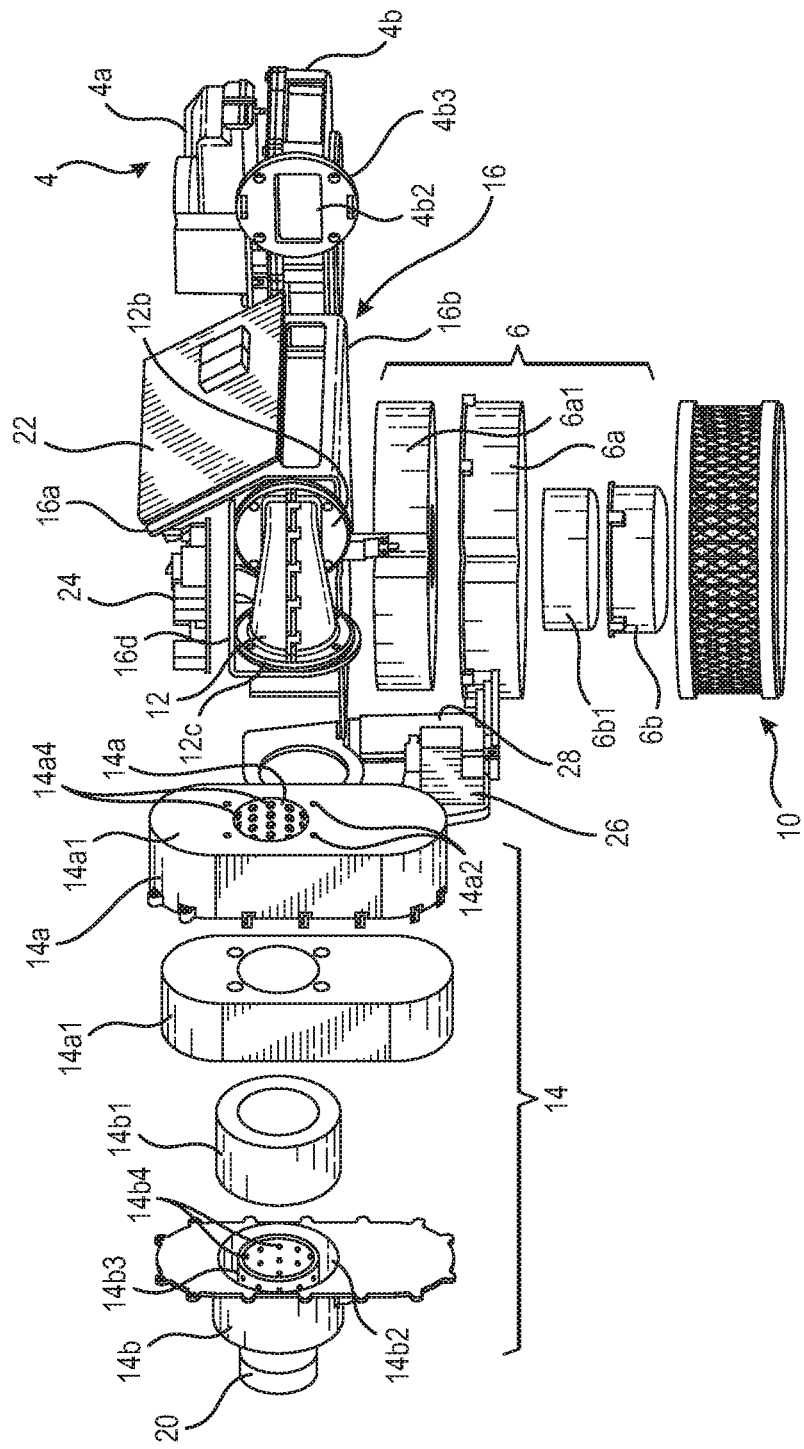
FIG. 7 shows the disassembled components of the inventive air convective warmer at a different perspective.

As best shown in FIGS. 3, 6 and 7, the motor assembly has a motor 4*a* and an impeller, or a fan, that is housed in an air plenum 4*b*. As is well known, the impeller is workingly coupled to motor 4*a* by means of a drive shaft (not shown) that extends from the motor. Thus, when the motor is energized, the impeller is rotated in air plenum 4*b*. The impeller for the motor assembly is a centrifugal fan and the motor assembly may be purchased from ebm-papst Landshut GmbH of Germany as Product No. RG148/1200-3612.

Air plenum 4*b* has an inlet and an outlet. Inlet 4*b*1 is best shown in FIG. 6. Outlet 4*b*2 (FIG. 7) is at the side of plenum 4*b* that faces inlet opening 12*a* of heater plenum 12, as per shown in FIG. 3. When mounted to base portion 16*a* of frame 16, the aperture opening at inlet 4*b*1 of air plenum 4*b* is aligned with opening 16*b*1 of frame 16 (FIG. 6). Thus, when motor 4*a* is energized, the impeller inside plenum 4*b* is rotated so that air is sucked into the cavity of plenum 4*b* via inlet 4*b*1 and a stream of pressurized airflow is output from outlet 4*b*2 of air plenum 4*b*.

Figure 5:
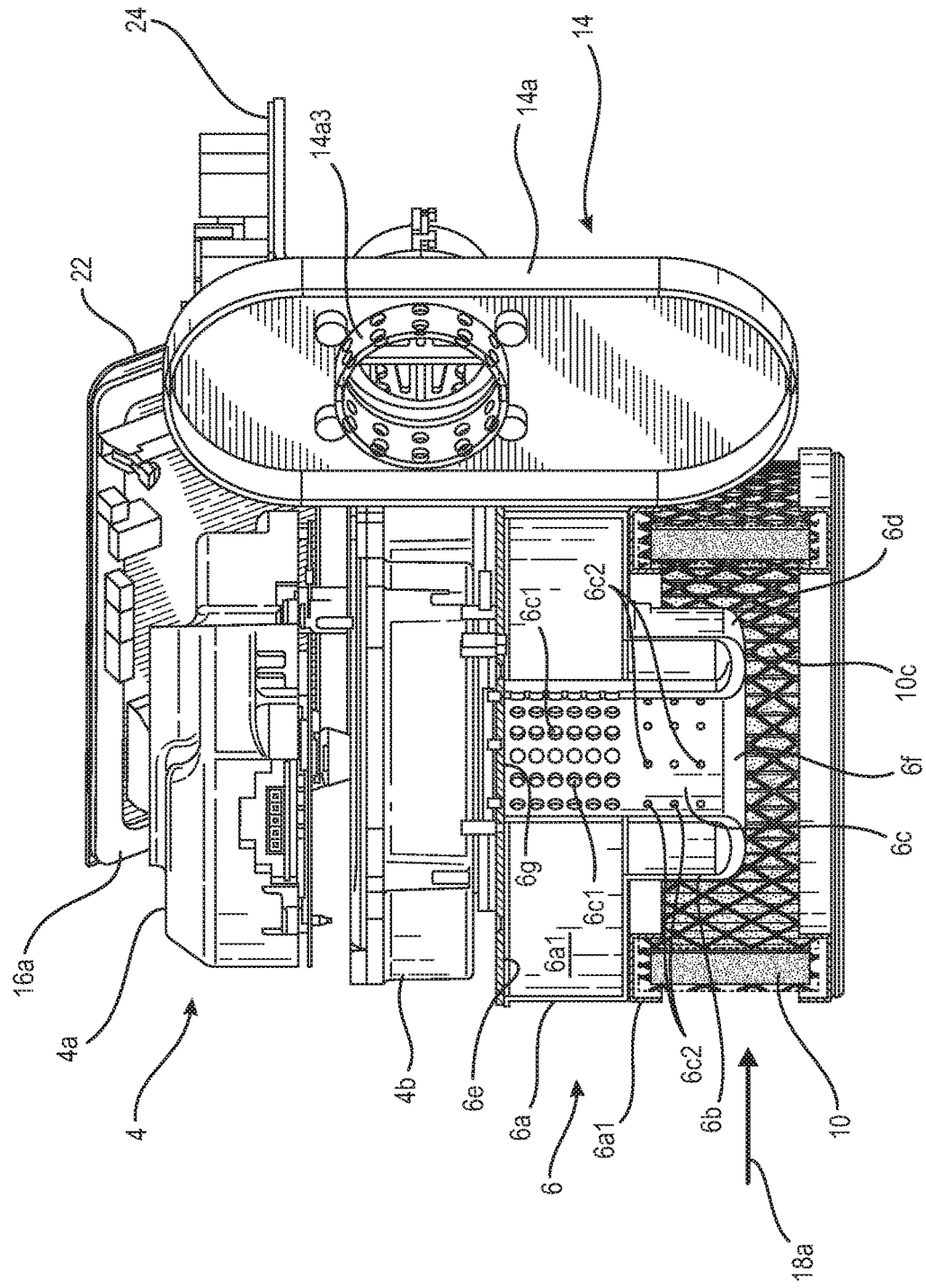
FIG. 5 shows cut away views of the inlet and outlet mufflers of the air convective warmer.

As shown in the figures, attached to the underside of base 16*b* of frame structure 16 is inlet muffler 6. As best shown in FIGS. 5-8, the exemplar embodiment inlet muffler 6 has two cylindrical sections 6*a* and 6*b*. For explanation purpose, sections 6*a* and 6*b* are shown to be separate elements in FIGS. 6 and 7, albeit sections 6*a* and 6*b* in actuality may be formed as sections of a one piece integral structure such as the inlet muffler 6 shown in FIG. 5. In any event, cylindrical section 6*a* is a wider section than section 6*b* and thus section 6*a* has a larger diameter than section 6*b*. The respective diameters and configurations of sections 6*a* and 6*b* are designed to enable those sections to attenuate or reduce noises of different frequency ranges. Larger diameter section 6a is designed to attenuate the lower frequency noises while smaller diameter section 6b is designed to attenuate noises of higher frequencies across the broadband of noise frequencies. As best shown in FIG. 5, sections 6a and 6b have a common central coaxial bore 6c that effects a through passage longitudinally along inlet muffler 6 between its lower end 6d and upper end 6e, where inlet 6f and outlet 6g, respectively, of inlet muffler 6 are located. Thus, a fluid communication path is established between air plenum 4b and the environment via the through passage as inlet 6f of inlet muffler 6 is positioned inside of and adapted to receive air filtered by filter 10. Given that outlet 6g is in alignment with inlet 4b1, when the motor assembly is in operation, the rotation of the impeller within plenum 4b creates a vacuum therein to suck filtered air from the environment into the air plenum 4b by way of inlet muffler 6.

The air that passes through the inlet muffler 6 into plenum 4b is filtered by filter 10. As shown in FIG. 5, filter 10 is removably coupled to the outer circumferential periphery of the underside of section 6a by a gasket 6a1, so that section 6b extends within cavity 10c of filter 10. Given that base 10b of filter 10 is air impermeable for the exemplar embodiment, the air being sucked into air plenum 4b through inlet muffler 6 flows into cavity 10c through the filter material of filter 10 in a sideways direction as indicated by directional arrow 18a.

To aid in the reduction of noise, section 6a and 6b of inlet muffler 6 each are fitted with a noise absorbent material 6a1 and 6b1, respectively, for the exemplar embodiment air blower as shown. The noise absorbent material may be a noise reduction foam purchased from the 3M company, or from the Acoustical Solutions company of Richmond, VA under the trade name AlphaComposite® acoustic foam. The foam may be formed as a pad that substantially form fits within each of the respective spaces defined between the outer walls of the sections and the inner circumferential wall of inlet muffler 6 that defines the common coaxial bore that forms through passage 6c To further enhance the reduction of noise, a plurality of apertures or holes are formed or provided at the inner circumferential or tubular wall of inlet muffler 6 that forms passage 6c. The size of the holes 6c1 at the inner circumferential wall that defines passage 6c at section 6a has a larger diameter than the diameter of the holes 6c2 at the circumferential wall that defines passage 6c at section 6b. The holes extend through the inner circumferential wall to noise absorbent foams 6a1 and 6b1 so that passage 6c is exposed to the noise absorbent foam. As a result, a portion of the noise resulting from the moving air traversing along passage 6c may be absorbed by the foam.

With the configuration of the inlet muffler 6 as shown, section 6a acts as a filter to attenuate the noises of lower frequencies that result from the turbulence of the air flow created by the movement of the impeller as the sucked in air moves through the air plenum. The noises of higher frequencies are attenuated by filter section 6b of inlet muffler 6. It should be appreciated that the various dimensions of the inlet muffler are dependent on the motor assembly, specifically the size of air plenum 4b and the rotational speed of the impeller that is required to generate the amount of airflow necessary to inflate a convective blanket connected to the outlet extension of the air convective warmer, as will be discussed below.

Although the inlet muffler 6 as discussed above has its high frequency attenuation section 6b fitted with a noise absorbent foam material, another embodiment of the inlet muffler requires the noise absorbent foam material be fitted to only one of the muffler sections, for example section 6a to attenuate the low frequency noise. For the high frequency noise attenuation, instead of fitted with a foam pad, section 6b may be configured as a Helmholtz chamber so that the resonance within the chamber acts to attenuate the high frequency noise. As is known, a Helmholtz chamber may be designed in accordance to the following.

For the inventive air blower, the inlet and outlet mufflers each may have a section configured as a Helmholtz chamber in the manner as illustrated above so that only the low noise frequency attenuation section of the inlet and outlet mufflers 6 is fitted with a noise absorbent foam material.

Figure 2:
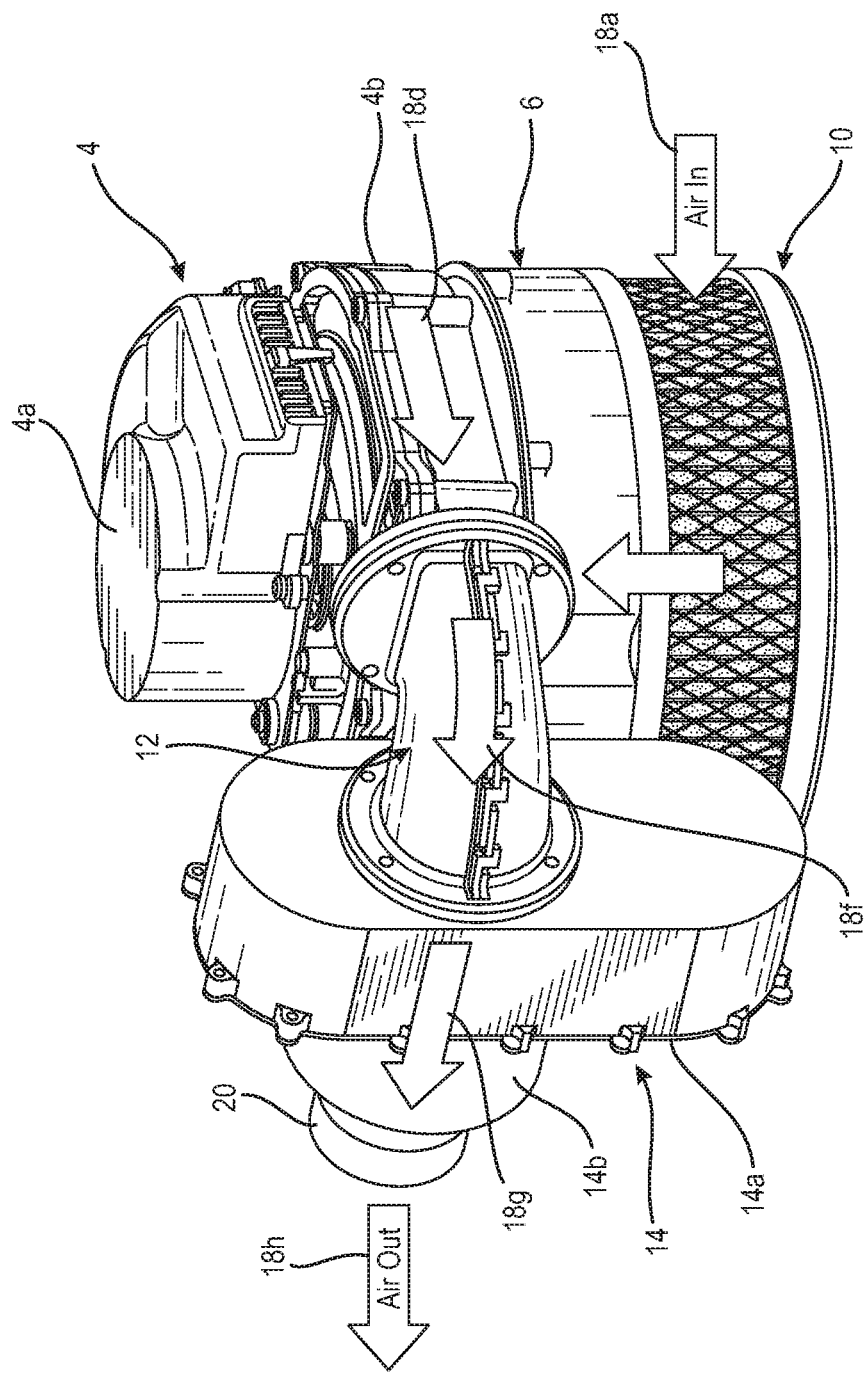
FIG. 2 is another perspective view of the inventive air convective warmer.

As best shown in FIGS. 2, 3 and 7, outlet 4b2 of air plenum 4b is coupled to inlet 12a of heater plenum 12 by means of an outlet flange 4b3 at plenum 4b and an inlet flange 12b of heater plenum 12. When coupled, outlet 4b2 is in alignment with inlet 12a to effect an airflow path, i.e., a fluid communication path, between air plenum 4b and heater plenum 12.

Figure 4:
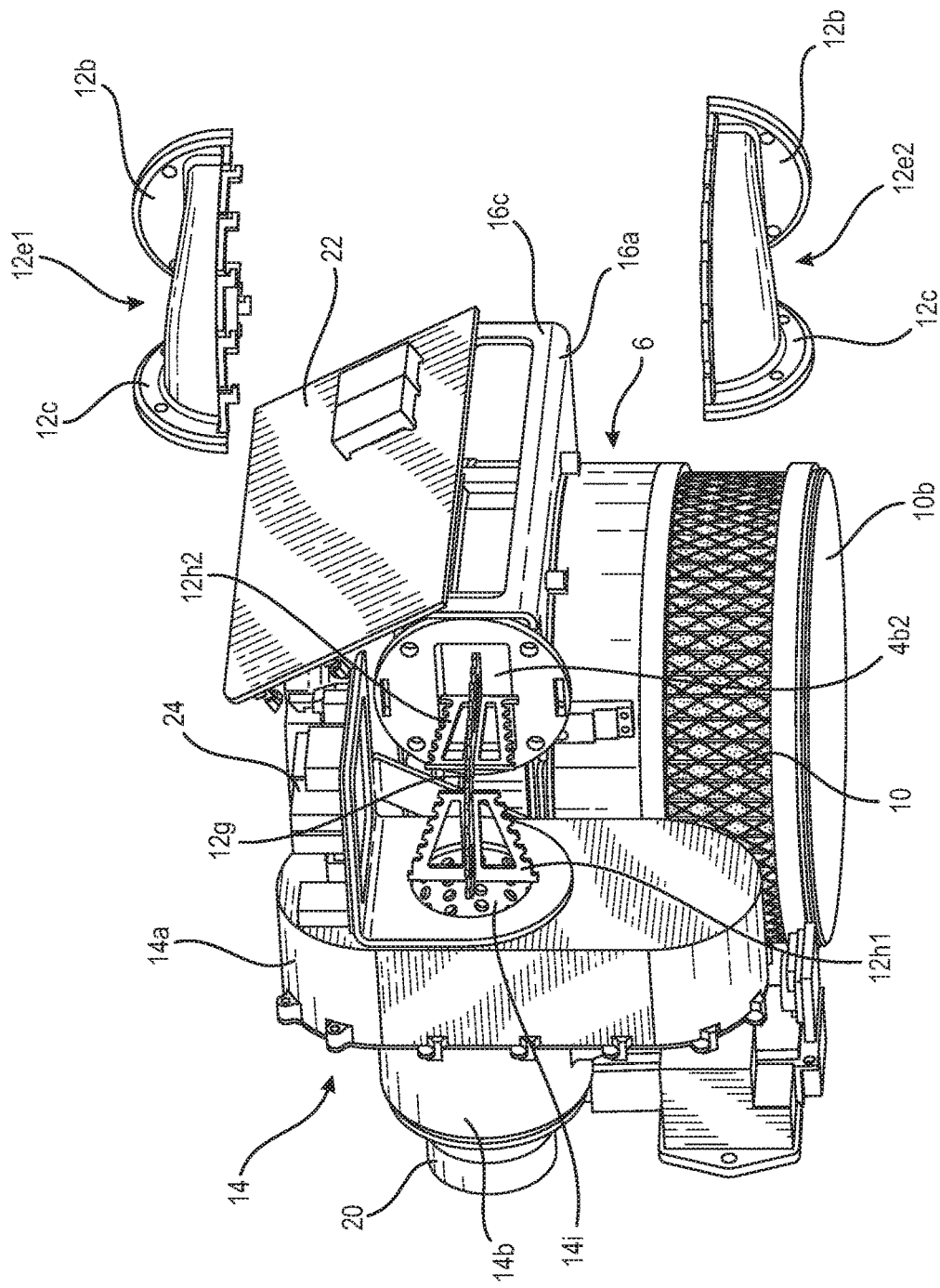
FIG. 4 is yet another perspective view of the air convective warmer where the housing of the heater plenum has been removed to show the heater elements.

Although heater plenum 12 shown in the figures is in the shape of an elbow for the exemplar embodiment air convective warmer, it should be appreciated that the heater plenum 12 may have other shapes. Heater plenum 12 is configured in the form of an elbow for the exemplar embodiment air convective warmer to effect a compact enclosure and to smooth out the turbulence of the airflow exiting plenum 4b. Provided inside heater plenum 12 are heater elements. In FIG. 4, the upper and lower portions 12e1 and 12e2 of the heater plenum are removed to one side of the figure to expose the heater elements, which may be heater coils 12h1 and 12h2 mounted to a support 12g. The air output from outlet 4b2 of air plenum 4b is heated by the heater elements in heater plenum 12 before exiting from outlet 12d (FIG. 8).

Figure 8:
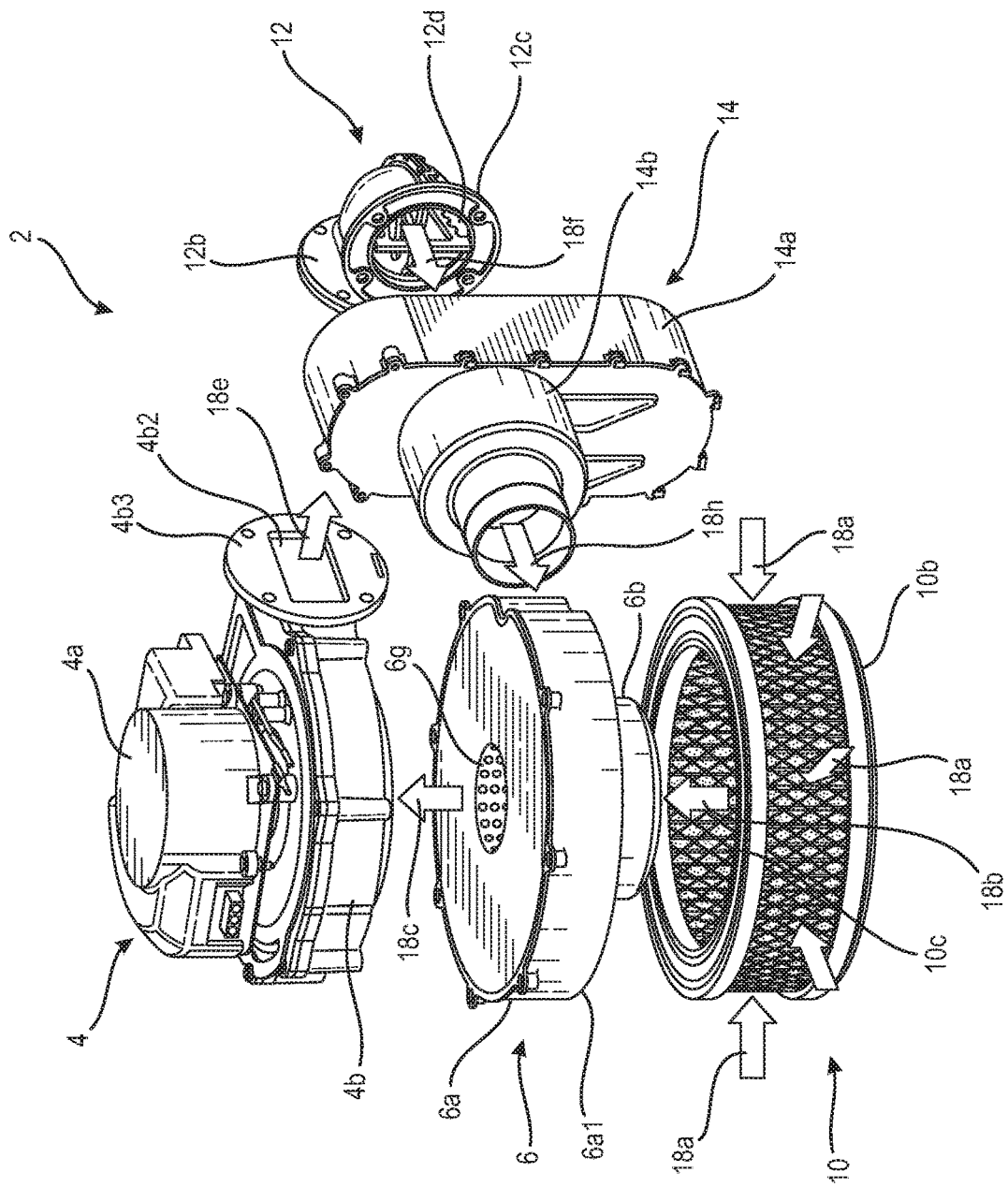
FIG. 8 is a semi-disassembled view of the air convective warmer showing the different major components thereof and the different airflow paths therethrough.

With reference to FIGS. 2 and 8, the output air is referenced by directional arrow 18d. The direction of the airflow from filter 10 into inlet muffler 6 is indicated by directional arrow 18b. The airflow from the outlet 6g of inlet muffler 6 to the inlet of air plenum 4b is indicated by directional arrow 18c. The movement of the airflow in air plenum 4b is indicated by directional airflow 18d. And the stream of airflow output from outlet 4b2 of air plenum 4b is designated by directional arrow 18e. It is this stream of pressurized airflow that is fed to heater plenum 12 as discussed above.

Outlet 12d of heater plenum 12 is in fluid communication with inlet 14i of the oblong section 14a of outlet muffler 14. As best shown in FIG. 7, an outlet flange 12e of heater plenum 12 is connected to an inlet surface 14a1 of oblong section 14a of outlet muffler 14 in a conventional known manner, as for example by rivets or screws. Alignment holes 14a2 are provided on inlet surface 14a1 so that inlet 14i of outlet muffler 14 may be correctly aligned with outlet 12d of heater plenum 12.

Outlet muffler 14 has a large oblong section 14a and a small cylindrical section 14b. Although shown to have an oblong structure, section 14a may be of other shapes including cylindrical. As shown in FIGS. 6 and 7, a noise absorbent foam pad 14a1 is fitted between tubular wall 14a3 and the outer wall of oblong section 14a, and a noise absorbent foam ring 14b2 is fitted between tubular wall 14b3 and the outer wall of cylindrical section 14b. Tubular walls 14a3 and 14b3 define the through passage for outlet muffler 14.

Same as the inlet muffler, there are holes along both of tubular walls 14a3 and 14b3 to expose the through passage to the noise absorbent foam to enhance noise reduction for outlet muffler 14. The holes 14a4 at tubular wall 14a3 have a larger diameter than the diameter of holes 14b4 at tubular wall 14b3. Similar to inlet muffler 6, larger section 14a attenuates the noise of the lower frequencies while smaller section 14b attenuates the noise of the higher frequencies of the air stream that passes through outlet muffler 14. Similar to inlet muffler 6, section 14b of outlet muffler 14 may be replaced by a Helmholtz chamber to attenuate the high frequency noises from the output airflow stream.

Although sections 14a and 14b of the outlet muffler 14 are shown as separate elements, in practice, both of those sections may be formed as a one piece integral component with the noise absorbent foam fitted therein, or a one piece integral component that includes a Helmholtz chamber. Both of the inlet and outlet mufflers may be molded as a one piece plastic component.

Integrated to the outlet side of section 14b of outlet muffler 14 is an outlet extension or coupler 20 adapted to connect to one end of an air hose, not shown, which other end is connected to a convective blanket, as is conventionally known, so that the convective blanket may be inflated by the stream of air output from the air convective warmer. Although not shown, outlet extension 20 may extend outside the housing that encloses the air convective warmer shown in FIGS. 1-8 for easy connection to the air hose. Outlet extension 20 may simply be referred to as the air outlet of the convective warmer that outputs the temperature regulated air, for example the air heated when it passes through the heater plenum 12. The stream of output air is referenced by directional arrow 18h shown in FIGS. 2 and 8.

A logic circuit board 22 mounted to frame section 16a of frame 16 provides the control to power the motor assembly as well as to energize the heating elements 12h1 and 12h2 for the convective air warmer. Circuit board 22 includes all of the low voltage electronics and microprocessor controllers, as well as the software needed to operate the air convective warmer. The software and electronics are well known and may be borrowed from the electronics that are used in the above-noted EQUATOR® air warmer. The circuit board also provides the electronics and circuits for a user or clinician to select the temperature for the output air. Sensors may be provided at the outlet extension 20 and/or the air hose to provide a feedback to maintain a regulated temperature of the air output from the air convective warmer. There is also a power circuit board 24 mounted to frame portion 16d. Power circuit board 24 has all of the power transistors, heat sinks and the power supply for providing the required voltage to control board 22, as well as the AC power that is needed to energize the heater elements 12h1 and 12h2 and motor 4a. The power to the heater elements is regulated by power circuit board 24 to control the temperature of the airflow being heated. A conventional power entry module 26 provides power to circuit board 24 from an electrical outlet. Further provided is a conventional regulated 24 volt power supply module 28.

With the inlet and outlet of the air plenum 4b of the motor assembly in fluid communication with the inlet muffler 6 and the outlet muffler 14, respectively, noises of both high and low frequencies are attenuated or reduced when air is output from the warmer to inflate a convective blanket at an optimum flow rate, for example at 38 cfm (cubic feet per minute). The outlet muffler also minimizes the turbulence and interference that is inherent in the stream of airflow from the blower, as well as the pressure drop of the output air stream. The noise level of the embodiment of the inventive air blower during operation is measured to be less than 43 dBA (sound pressure level), which is a reduction in noise from the above-noted EQUATOR® convective warmer.

Figure 9:
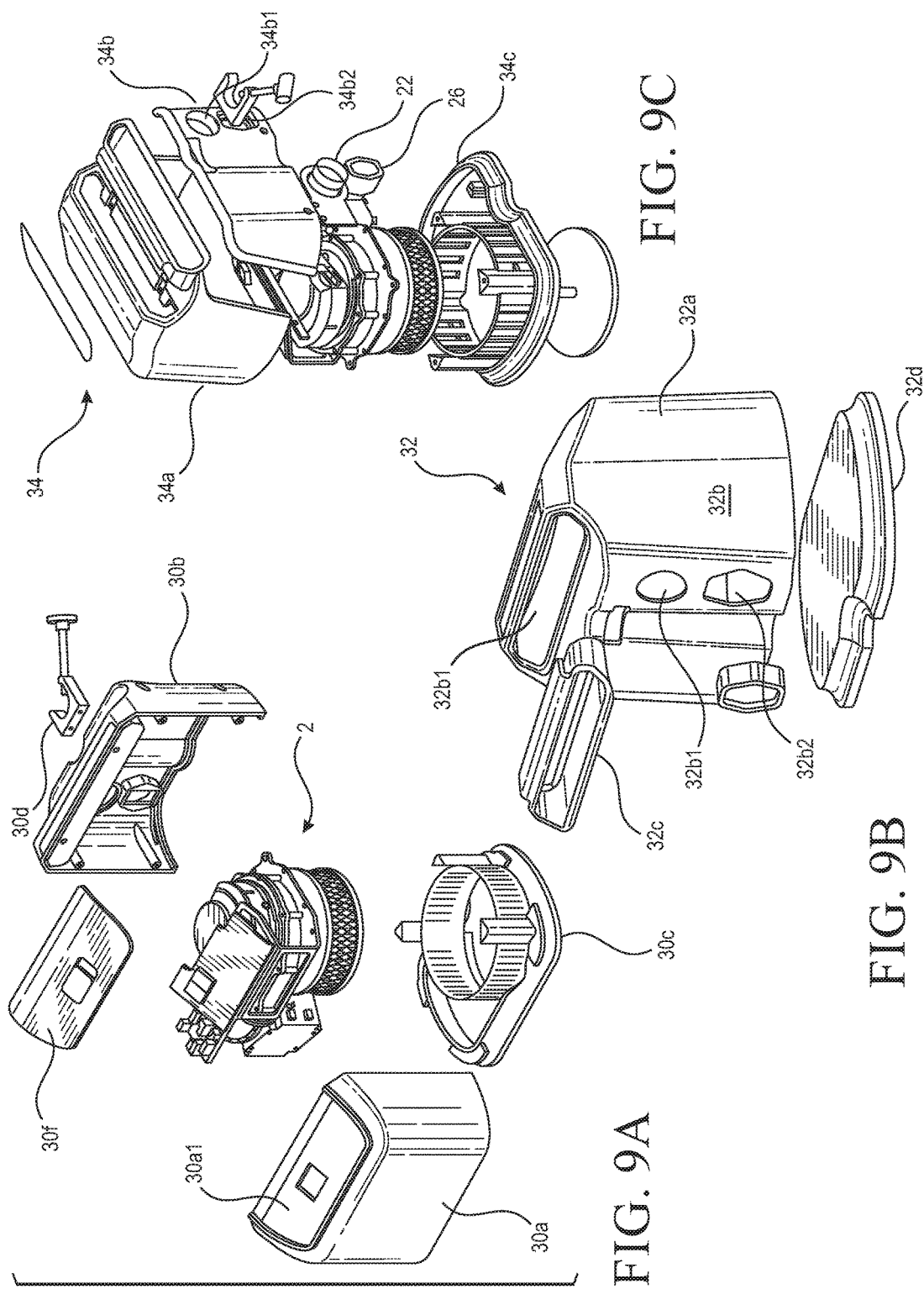
FIGS. 9A, 9B and 9C are exemplar housings to encase the inventive air convective warmer.

FIGS. 9A-9C are exemplar housings that may be used to enclose air convective warmer 2. The housing in FIG. 9A is made up of a front half casing 30a and a back half casing 30b as well as a base 30c onto which filter 10 is placed. To the back of casing 30b there may be added a mechanism 30d to enable the housing to be held onto a pole of a stand, not shown. A faceplate 30f that may be placed onto the viewing surface 30a1 at the front half casing 30a to provide the display and interface means for the user to view and interact with the convective warmer, for example setting the required temperature and alarm limits as is well known. FIG. 9B shows another exemplar housing 32 that may be used to house the inventive air convective warmer. Housing 32 also has a front casing 32a, a back casing 32b, a rear insert 32c to fit over an opening 32b1 of the casing as well as a base 32d. FIG. 9C shows yet another exemplar housing 34 having at its front casing 34a and back casing 34b superposed over the air convective warmer, as well as a base 34c for supporting the air convective warmer. Openings 34b1 and 34b2 in the back casing 34b are for outlet extension 22 and power entry module 26. The same types of openings are shown as 32b1 and 32b2 in the FIG. 9B embodiment. Similar openings are shown in the back casing 30b of the FIG. 9A embodiment housing. The respective peripheries for each of the bases 30c, 32d and 34c curve inwardly in an upward manner toward the platform of the bases where the air filter is positioned. In the exemplar embodiments of FIGS. 9A and 9C, the filter is positioned within a circumferential picket fence cage integrally extending upwardly from the base. The curved shape of the periphery of each of the bases provides a smoother inlet to the air plenum and therefore contributes to the attenuation or reduction of the noise of the air being sucked into the filter and then into the air plenum. As a result, the noise level of the air intake at the air inlet for the air warmer housed in the exemplar housings is low. This low noise air intake in turn contributes in keeping the noise level of the inventive air warmer low. An additional advantage of the base having an upwardly and inwardly curved periphery is that it keeps away water ingress to the housing of the air warmer.

Figure 10:
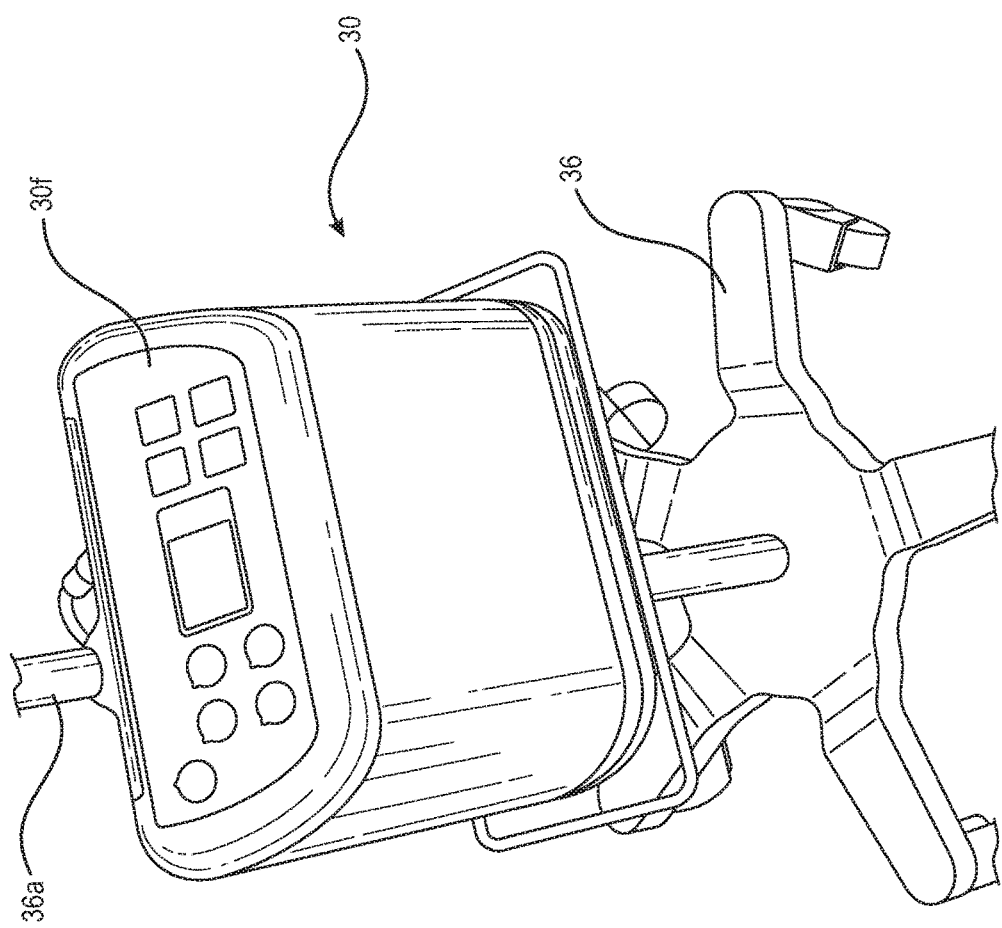
FIG. 10 shows a fully assembled inventive air convective warmer on a stand.

FIG. 10 shows the inventive air convective warmer housed in the exemplar FIG. 9A housing mounted to a pole 36a of a stand 36. For the exemplar housing of FIG. 10, face 30f at the front casing shows the temperature of output air, the various inlet and outlet temperature set, as well as the power switch and other displays that assist a clinician in the use of the inventive air convective warmer.

Figure 11:
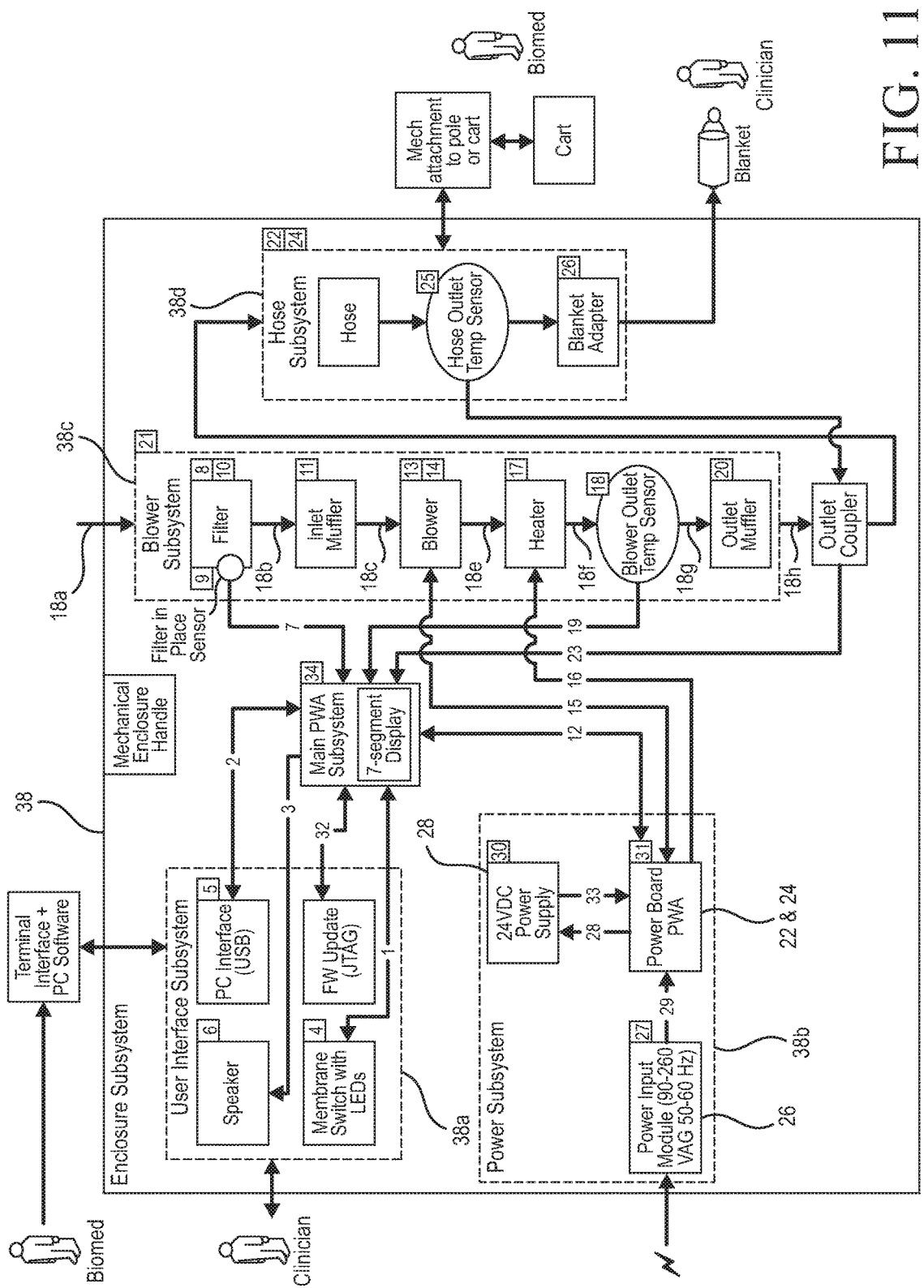
FIG. 11 is an illustration of the system architecture of the inventive air convective warmer and its use.

FIG. 11 is a system architecture drawing that shows an overall view of the inventive air convective warmer vis-a-vis the convective blanket. As shown, the housing is identified as the enclosure subsystem with the user interface subsystem and the power subsystem in dotted line boxes. The enclosure subsystem 38 may be equated to the exemplar housing 30 shown in FIG. 10 with the user interface subsystem 38a corresponding to the faceplate 30f. The power subsystem 38b is a combination of the power input module 26, the power supply 28, the circuit board 22 and the power board 24. The filter 10, the inlet muffler 6, the motor assembly (designated as the blower), the heater plenum (designated as the heater), and the outlet blower are shown in the blower subsystem 38c. The air flow, referenced by directional arrows 18a-18h, are also shown in the blower subsystem 38c. The stream of air output from the convective warmer is sent to the hose subsystem 38d, which includes the air hose, to connect to the outlet extension 20. In essence, the hose subsystem 38d is an air hose that may include sensors for providing feedback to the controller at circuit board 22 to control the temperature of the airflow being output to inflate the blanket. The sensors may be used as part of a built-in reference circuit to allow different types of air hoses to be coupled to the air warmer without the need to re-calibrate the air warmer. The built-in reference circuit will be discussed below with reference to FIG. 13.

Figure 12A:
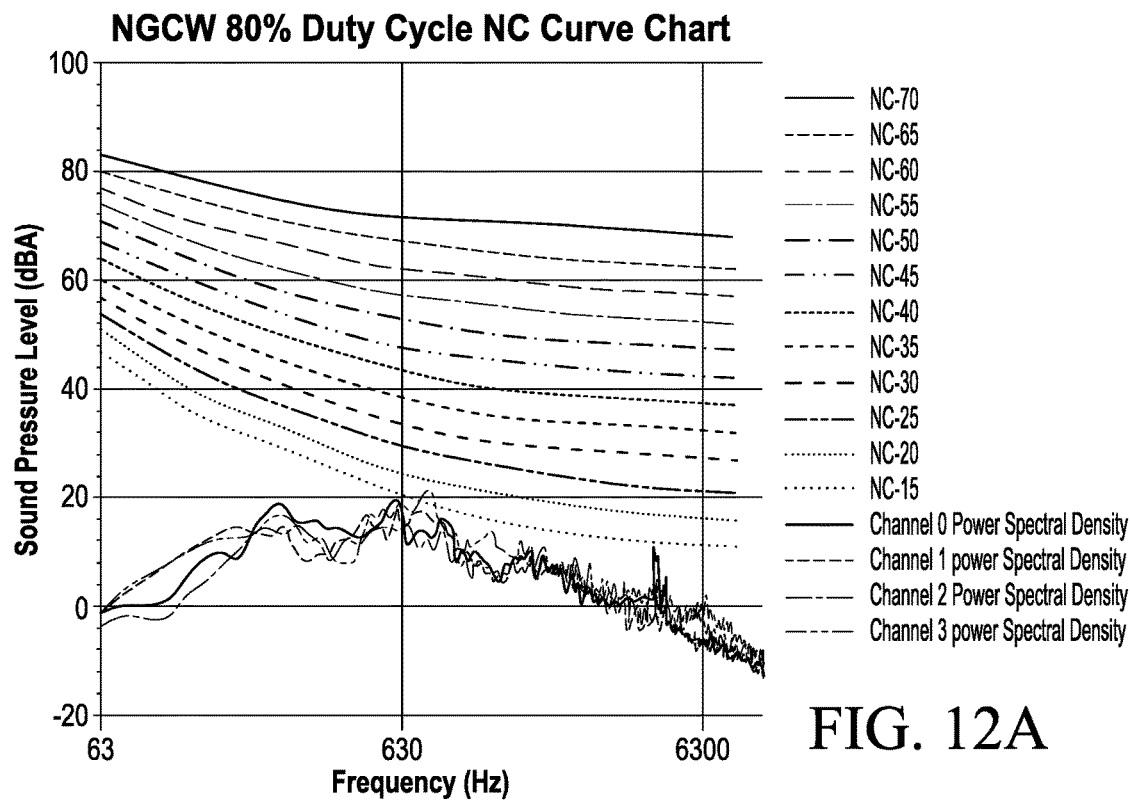
FIGS. 12A and 12B are NC (noise criteria) and NR (noise rating) charts showing the noise level generated by the inventive air convective warmer.
Figure 12B:
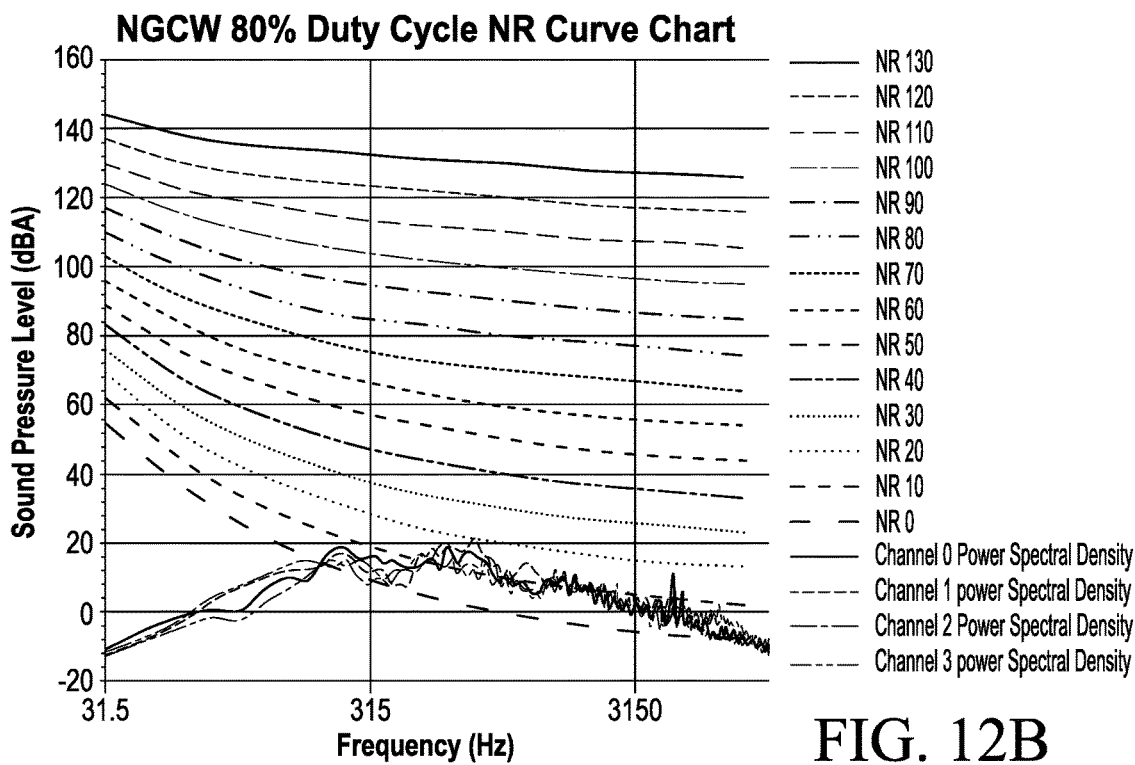

FIGS. 12A and 12B are charts illustrating the sound quality of the inventive warm air blower. These charts describe the measured noise level having taken into account the frequency content of the noise. FIG. 12A is a NC (Noise Criteria) curve chart while FIG. 12B is a NR (Noise Rating) curve chart each showing the noise level generated by the inventive air blower operating at 80% duty cycle. The FIG. 12A NC chart was first developed in the late 1950's and is commonly used in the United States. The FIG. 12B NR chart is based on the ANSI Standard S 12.2-1995 and is commonly used in Europe. As can be seen, the sound level dBA vis-a-vis the frequencies resulting from the operation of the air warmer of the instant invention at a duty cycle of 80% is approximately at or below 20 dBA for both the NC and NR charts. It has been determined that the inventive blower operating at 80% duty cycle is fully capable of inflating most, if not all, of conventional convective blankets including those sold by the assignee of the instant application.

The level of noise, or simply noise, of the air blower of the instant invention, which may technically be referred to as the Leq (Equivalent continuous sound level) Average Sound Levels (or simply dBA), was measured under different sets of conditions whereby components were added as well as removed from the overall air blower. For example, different levels of noise resulting from the operation of the air blower were measured with the inlet muffler and/or the outlet muffler removed, only one of the mufflers removed, and the shapes of the respective portions of each of the inlet and outlet mufflers reconfigured. Also, different types of noise insulating or reduction materials (or no material) were fitted, form fitted or otherwise, within each of the inlet and outlet mufflers, either separately or together, to determine the amount of noise reduced by the use of those materials. Some of the sound insulating foam materials used include Basotect G+ from the BASF company, polyurethane 2 Ib, polyurethane 4 Ib, 3M Thinsulate, as well as air (no material). The same foam material may be used in both of the inlet and outlet mufflers, or different foam materials may be separately used in the mufflers.

By varying the configuration of the mufflers as well as fitting the mufflers with the different types of sound reduction material discussed above, the level of noise, i.e., dBA, resulting from the operation of the air blower of the instant invention based on the configuration of the mufflers as discussed above is determined to be confined to between approximately 44.5 dBA (air with no sound reduction material) to approximately 41 dBA (with Basotect G+). With all components added to the air blower including the air filter and the heater fixedly positioned within the elbow of the air blower as described above, the level of noise when the inventive air blower is in operation is measured to be between approximately 42 dBA and 43 dBA. A noise level of approximately 42.6 dBA was measured over time with the inventive air blower in continuous operation.

As discussed above, sensors are provided at the outlet extension 20 as well as the air hose to provide a feedback to maintain a regulated temperature of the air output from the air convective warmer. For the instant invention, there is also provided a built-in sensor (or thermistor) reference circuit that allows the clinician to switch to different types of air hoses, for example switching from an air hose used to inflate an adult blanket to an air hose used to inflate a pediatric blanket, without having to re-calibrate the air warmer to take into account the different dimensions of the blankets, as well as the different air hoses used to establish a fluid flow path between the blankets and the air convective warmer. The built-in reference circuit utilizes the sensors provided at the patient end of the air hose and the sensor provided at the outlet of the convective warmer. One such configuration of the placement of the sensors is described in U.S. Pat. No. 6,143,020, assigned to the assignee of the instant application. In the '020 patent, two sensors are mounted to a cross structure attached to the patient end of the air hose to provide a temperature feedback to the air warmer. The sensors are conventional temperature sensing devices such as thermocouples, thermistor or resistive temperature devices (RTD), semi-conductor diode-junction or integrated circuit temperature sensors.

Figure 13:
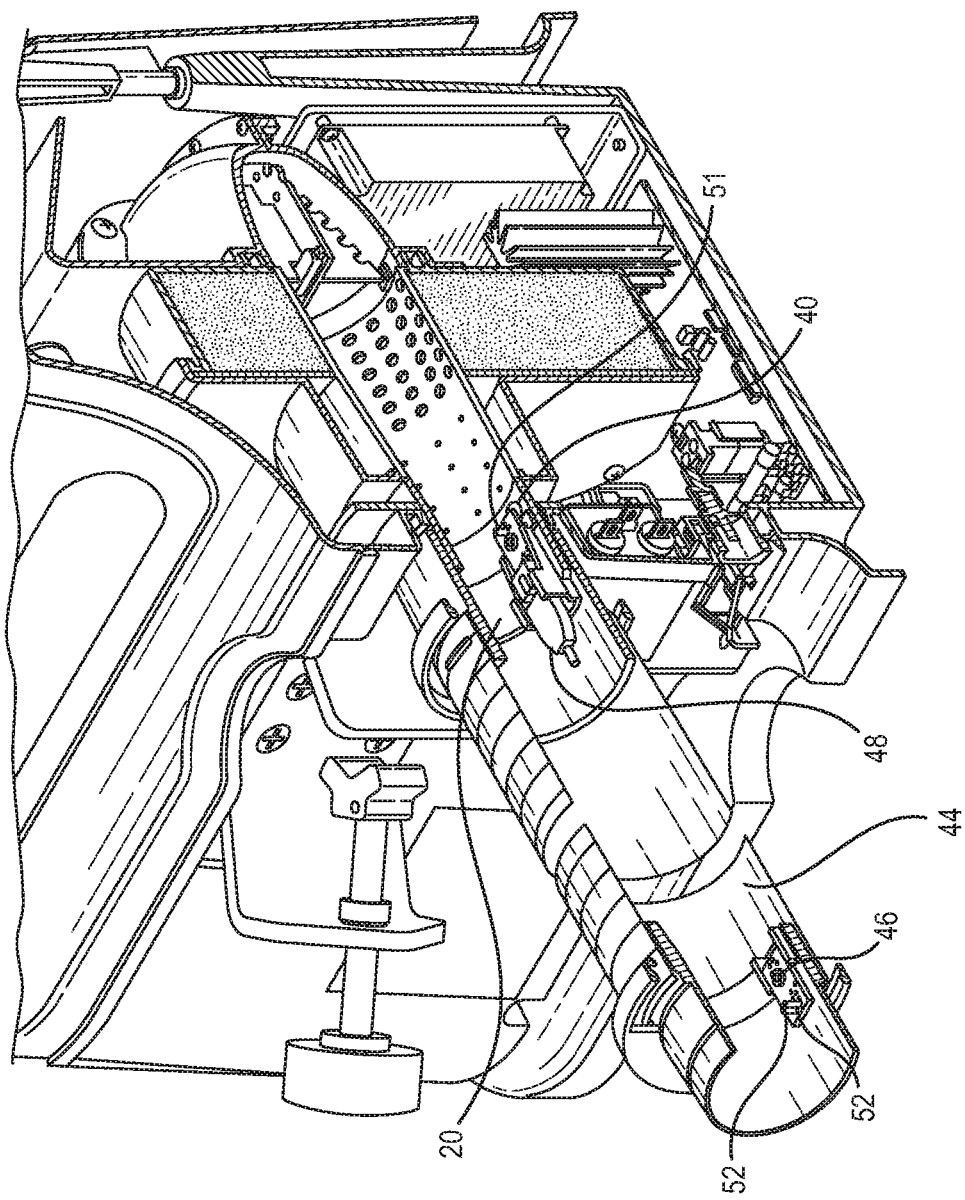
FIG. 13 is an illustration showing an exemplar positioning of the sensors at the hose and the outlet of the air convective warmer that may be used to provide a built-in sensor reference circuitry to enable different types of air hoses to be used with the air convective warmer without the need to re-calibrate the warmer for each type of the air hoses.
Figure 14:
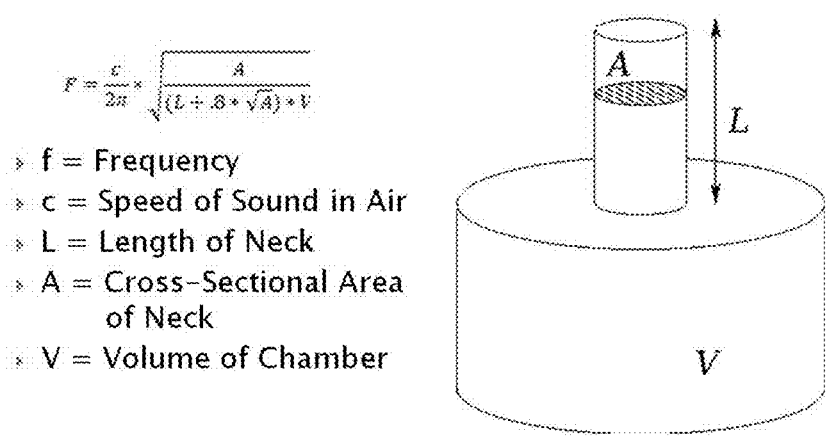
FIG. 14 is an illustration of a Helmholtz chamber that may be designed in accordance to the noted formula.
Figure 15:
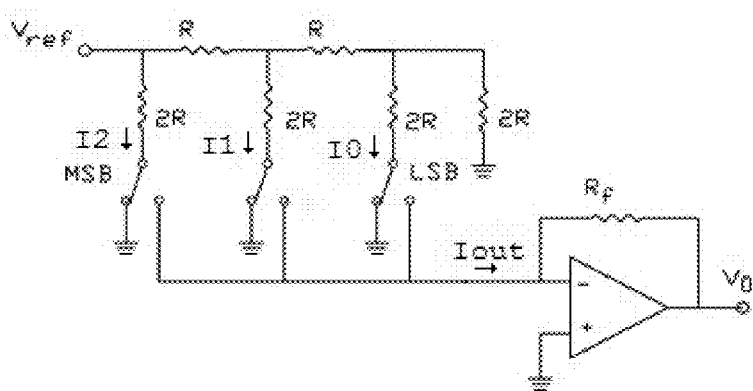
FIG. 15 is an illustration of a resister ladder scheme to establish a number of outputs that correspond to different types of air hoses.

FIG. 13 is an illustration of an alternate exemplar sensor configuration for providing a feedback to control the temperature of the air output from the air convective warmer. As shown, a circuit board 40 supporting a sensor S1 is mounted at the outlet extension 20 of the air convective warmer. Mounted to the patient end of air hose 44 is another circuit board 46 that has mounted thereto two sensors S2 and S2'. Each of sensors S2 and S2' operates to measure the temperature of the heated air output from the convective warmer. Having two sensors provides redundancy to the system. As further shown, a connector 48 connected to the circuit board 40 represents the electrical connection between the circuit boards 40 and 46 that enables the temperature at the end of the air hose measured by sensors S2 and S2' to be fed to circuit board 40 as a remote temperature signal. As should be appreciated, the temperature at the patient end of the air hose corresponds to the temperature of the air being input to inflate the blanket. By way of circuit board 40, signals representing the air temperature measured at the patient end of the air hose and the temperature of the heated air measured at the outlet of the air blower by sensor S1 are sent to the control system 38 of the air warmer. Based on the difference of the temperatures at the outlet of the warmer and at the patient end of the hose, a feedback is provided to the control system 38 to maintain regulate a desired temperature for the air output from the air convective warmer.

In addition to providing a feedback, the inventive air convective warmer has a built-in reference circuit that enables the warmer to use the aforenoted sensors to automatically sense the air hose that is connected to the warmer, for example whether it is an air hose used for inflating an adult underbody blanket or an air hose used to inflate a pediatric blanket. The circuit utilizes the sensors to establish an output table by applying a linear calibration to the existing values of the sensors with reference to the different types of air hoses that may be used with the air convective warmer for inflating the different convective blankets.

One example of utilizing the values of the different sensors (or thermistors) is by using a resistor ladder scheme, for example a R-2R network to establish a number of outputs that respectively correspond to the different types of air hoses. Thus, when a given air hose is coupled to the air warmer, an output that corresponds to the characteristics of the given air hose is provided to the controller of the air warmer to automatically adjust the rate and amount of heated air to output from the air warmer, i.e., to effect a substantially optimal air output for the given air hose. The respective characteristics of the different air hoses may be measured empirically. An exemplar R-2R network circuit adapted to provide eight outputs is shown hereinbelow.

Eight outputs are believed to be adequate to accommodate the different air hoses that are adapted to be used with the inventive air convective warmer. However, if there are additional types of air hoses and thus additional outputs are required, additional resistance series may be added to the circuit to provide outputs of 10, 12, 14, etc.

The above exemplar R-2R network circuit can be seen to be like a current source whose output depends on switch setting B2, B1, B0 (MSB to LSB) that controls I2, I1, I0 respectively.

$$I_{out}=V_{ref}\times 8R(4B2+2B1+B0) \quad (1)$$

Including the op amp which behaves like I-V converter, the voltage output can be obtained per the following equation.

$$V_{out}=V_{ref}\times R_f\times 8R(4B2+2B1+B0)$$

Letting $V_{ref}=1$ and $R_f=2R$, the following output table is obtained.

Output Table

| B2 | B1 | B0 | Digital Value | $V_{out}$ |
|---|---|---|---|---|
| 0 | 0 | 0 | 0 | 0 |
| 0 | 0 | 1 | 1 | −0.25 |
| 0 | 1 | 0 | 2 | −0.5 |
| 0 | 1 | 1 | 3 | −0.75 |
| 1 | 0 | 0 | 4 | −1.0 |
| 1 | 0 | 1 | 5 | −1.25 |
| 1 | 1 | 0 | 6 | −1.5 |
| 1 | 1 | 1 | 7 | −1.75 |

As the R-2R network circuit is well known and equations (1) and (2) are likewise well known, it suffices to note that the above R-2R circuit acts to provide different values, in this instance eight, that are adapted to correspond to the different characteristics of the different air hoses. For example, value "1" having the exemplar output voltage of −0.25 may be construed to correspond to the coupling to the inventive air warmer of an air hose optimally adapted to be used to inflate an adult blanket, for example the adult underbody blanket SWU-2119 sold by the assignee of the instant application. Value "2", which corresponds to an exemplar output voltage of −0.5, may be construed to mean that an air hose coupled to the inventive air convective warmer is to be used to inflate an underbody pediatric blanket, for example the pediatric underbody blanket SW-2009 sold by the assignee of the instant application. This correspondence of the value outputs from the above R-2R circuit therefore provides a built-in table for the controller of the air convective warmer to automatically and optimally adjust its air output to accommodate the air hose connected to the warmer. For example, when an air hose for inflating the exemplar adult SWU-2119 blanket is connected to the inventive air warmer, the controller of the air warmer would effect the blower to output air at a highest rate of about 2236 ft/min (approximately 52 CFM (Cubic Feet per Minute)). For the exemplar pediatric SW-2009blanket, the controller of the air warmer would effect the blower to output the heated air at a lowest rate of about 2026 ft/min (approximately 47 CFM). The rate of the air output from the air warmer may be manually adjusted by the clinician if needed.

For the exemplar R-2R circuit, 15° C. may be used as a first reference temperature and 44° C. may be used as the second reference temperature to compensate for the thermistor values, so that the output voltages in practice may be different from those shown in the table. With the built-in reference circuit, a clinician can switch air hoses to connect different convective blankets to the inventive air convective warmer without having to re-calibrate the air output from the air warmer. Another advantage of the built-in reference circuit is that it also removes the need to have any annual or bi-annual calibration of the air warmer, as the air output is calibrated automatically in accordance with the values of the output table. Yet another advantage is that the built-in circuit does not require additional components, insofar as it utilizes the existing senors.

Inasmuch as the present invention is subject to variations, modification and changes in detail, it is intended that all matters described throughout this specification and shown in the accompanying drawings be interpreted as illustrative only and not in a limiting sense. For example, instead of the oblong configuration for the large section of the outlet muffler, that section of the outlet muffler may be configured in a cylindrical configuration to reduce air turbulence. So, too, instead of fitting a noise absorbent foam in at least one of the sections in each of the mufflers, with the proper design, both sections of the inlet and outlet mufflers may be configured as Helmholtz chambers. Alternatively, a different type of noise absorbent material other than foam may be used to enhance the reduction of noise during the operation of the warmer. Accordingly, it is intended that the invention be limited only the spirit and scope of the hereto appended claims.

The invention claimed is:

1. An air blower comprising:
a plenum wherein an impeller is movably positioned, the plenum having an inlet and an outlet;
a motor working cooperatively with the impeller for rotating the impeller;
an inlet noise reduction structure positioned relative to the plenum including a housing having one wide section having a first diameter and one narrow section having a second diameter that is smaller than the first diameter, the wide section and the narrow section forming a common coaxial bore that effects an inlet through passage longitudinally along the inlet noise reduction structure, the one wide section positioned adjacent to the plenum so that an outlet of the inlet through passage is in fluid communication with the inlet of the plenum to establish a fluid communication path between the inlet through passage and the plenum, a noise absorbent material fitted to at least one of the wide and narrow sections to surround a corresponding portion of the inlet through passage;
wherein when the motor is activated, the impeller is rotated to draw air into the plenum from the inlet through passage and to output a stream of air flow through the outlet of the plenum;
wherein a portion of noise resulting from the movement of air in the plenum is reduced by the inlet noise reduction structure;
wherein the wide section is defined by a wide outer circumferential wall having a diameter and the narrow section is defined by a narrow outer circumferential wall that has another diameter smaller than the diameter of the wide outer circumferential wall, a circumferential flange formed where the wide section meets the narrow section, the air blower further comprising:
an air filter removably attached to the circumferential flange, the filter including a circumferential air passable barrier defining a cavity encircling the narrow section;

wherein air is drawn into the cavity when the air blower is in operation.

2. The air blower of claim 1, further comprising:
an outlet noise reduction structure including a housing having at least a large section and a small section encircling an outlet through passage, the large section positioned relative to the plenum so that another fluid communication path is established between an inlet of the outlet through passage and the plenum, a noise absorbent material fitted to at least one of the large and small sections to surround a corresponding portion of the outlet through passage;
wherein the outlet noise reduction structure together with the inlet noise reduction structure substantially reduce the noise resulting from the movement of air through the plenum.

3. The air blower of claim 2, wherein the inlet through passage is defined by a circumferential wall that extends internally along the wide and narrow sections, a plurality of holes formed along the circumferential wall, the holes at the circumferential wall along the wide section having a larger dimension than the holes at the circumferential wall along the narrow section;
wherein the outlet through passage is defined by an other circumferential wall that extends internally along the large and small sections, a plurality of holes formed along the other circumferential wall, the holes at the other circumferential wall along the large section having a larger dimension than the holes at the other circumferential wall along the small section.

4. The air blower of claim 2, wherein each of the wide and narrow sections of the inlet noise reduction structure is fitted with the noise absorbent material; and
wherein each of the large and small sections of the outlet noise reduction structure is fitted with the noise reduction material;
whereby the noise resulting from the operation of the air blower is measured to be in a range of approximately 41 dBA to 44.5 dBA.

5. The air blower of claim 1, further comprising at least one heater element positioned relative to the outlet of the plenum to heat the air flow output from the outlet of the plenum.

6. The air blower of claim 2, further comprising a heater plenum wherein at least one heater element is positioned, the heater plenum interposed between the plenum and the outlet noise reduction structure, the heater plenum having an inlet to receive the air output from the plenum and an outlet to output the air having been heated by the heater element to the inlet of the outlet noise reduction structure so that heated air is output from the outlet of the outlet through passage; and
wherein the outlet noise reduction structure includes an outlet extension adapted to connect to one end of an air hose which other end is connectable to a convective blanket so that the blanket may be inflated by the heated air output from the outlet noise reduction structure.

7. The air blower of claim 4, wherein the inlet through passage is formed by a first internal circumferential wall that extends along the wide and narrow sections,
wherein the outlet through passage is formed by a second internal circumferential wall that extends along the large and small sections; and
wherein the first and second internal circumferential wall each are circumscribed by the noise absorbent material.

8. The air blower of claim 1, wherein the inlet through passage is formed within the housing of the inlet noise reduction structure;
wherein one of the wide and narrow sections of the housing is fitted with the noise absorbent material and other of the wide and narrow sections is a Helmholtz chamber; and
wherein the one of the wide and narrow sections of the housing fitted with the noise absorbent material attenuates low frequency noise and the Helmholtz chamber attenuates high frequency noise.

9. The air blower of claim 2, wherein the outlet through passage is formed within the large and small sections of the housing of the outlet noise reduction structure;
wherein one of the large and small sections of the housing is fitted with the noise absorbent material and other of the large and small sections is a Helmholtz chamber;
wherein the noise absorbent fitted section attenuates low frequency noise and the Helmholtz chamber attenuates high frequency noise.

10. The air blower of claim 1, further comprising an air outlet adapted to couple to different types of air hoses each having provided at its patient end at least one sensor, at least an other sensor provided at the air outlet of the air blower, the at least one sensor measuring the temperature of air heated by a heater element at the patient end of an air hose coupled to the air outlet and the at least other sensor measuring the temperature of air at the air outlet, a circuit that utilizes the values of the one and other sensors with reference values to establish a reference table of stepped values that correspond to each type of the different types of air hoses adapted to be coupled to the air outlet, wherein when a given air hose is coupled to the air outlet, the circuit effects the motor to rotate the impeller at a rate in accordance to a step value that corresponds to the type of air hose said given air hose is.

11. An air blower, comprising:
a motor assembly including a motor, a plenum and an impeller movably positioned inside the plenum workingly coupled to the motor, the plenum having an inlet and an outlet;
an air filter through which air is sucked into the plenum when the motor assembly is in operation;
an inlet muffler coupled to the plenum at its one end and the air filter at its other end, the inlet muffler including a first housing having an outer wall and a circumferential inner wall enclosing an inlet through passage, the inlet through passage establishing a fluid communication path between the inlet of the plenum and the air filter, a sound absorbent material fitted between the outer wall and the inner wall of the first housing;
an outlet muffler including a second housing having an outer wall and an inner circumferential wall defining an outlet through passage, the outlet muffler positioned relative to the plenum with the outlet through passage in fluid communication with the outlet of the plenum, a sound absorbent material fitted between the outer wall and the inner wall of the second housing;
wherein when the motor assembly is in operation, air is sucked into the inlet through passage through the air filter, passes to the plenum and outputs therefrom to the outlet through passage as a stream of air flow; and
wherein sound resulting at least from air turbulence due to movement of the air in the plenum during operation of the motor assembly is reduced by the inlet and outlet mufflers, wherein the air blower further comprises a heater plenum having at least one heater element interposed between the plenum and the outlet muffler, the heater plenum routing the air output from the plenum to the outlet muffler, the heater plenum structurally configured to reduce the turbulence of the being routed air, the air in the heater plenum being heated by the at least one heater element so that heated air is output to the outlet muffler; and wherein the outlet muffler includes an outlet extension adapted to connect to one end of an air hose which other end is connectable to a convective blanket so that the convective blanket may be inflated by the heated air output from the outlet muffler.

12. The air blower of claim 11, wherein the air hose has at least one sensor at its patient end and the outlet extension has at least an other sensor, further comprising a circuit that utilizes values of the one and other sensors with reference values to establish a set of stepped values that correspond to each type of different types of air hoses adapted to be coupled to the outlet extension, wherein when a given air hose is coupled to the outlet extension, the circuit effects the motor to rotate the impeller at a rate in accordance to a step value that corresponds to the type of air hose said given air hose is.

13. An air blower, comprising:
a motor assembly including a motor, a plenum and an impeller workingly coupled to the motor movably positioned inside the plenum, the plenum having an inlet and an outlet;
an air filter;
an inlet muffler including an inlet through passage in fluid communication with the inlet of the plenum and the air filter, an inlet low frequency noise attenuation section and an inlet high frequency attenuation section;
an outlet muffler including an outlet through passage in fluid communication with the outlet of the plenum, an outlet low frequency noise attenuation section and an outlet high frequency attenuation section;
wherein when the motor is activated to rotate the impeller in the plenum, air is sucked through the air filter into the inlet muffler and a stream of air flow is output from the outlet muffler; and
wherein the inlet and outlet mufflers act to reduce noise resulting from operation of the air blower,
wherein the air blower further comprises:
a heater plenum interposed between the outlet of the plenum and the outlet muffler to provide a conduit for the air flow from the plenum to the outlet muffler, at least one heater positioned inside the heater plenum to heat the air flowing through the heater plenum so that heated air is output to the outlet muffler, the heater plenum configured to have a structure that reduces the turbulence of the air flow passing therethrough.

14. The air blower of claim 13, wherein the noise resulting from the operation of the air blower is measured to be between approximately 42 dBA to 43 dBA.

15. The air blower of claim 13, further comprising:
a casing for housing at least the motor assembly, the inlet and outlet mufflers and the plenum; and
wherein the noise resulting from the operation of the air blower is measured at approximately 42.6 dBA.

16. The air blower of claim 13, wherein the inlet and outlet through passages are defined by respective circumferential walls internal of the inlet and outlet mufflers, respectively, a plurality of holes formed along the respective walls of each of the through passages, the dimension of the holes in the low frequency attenuation section of the through passages being different from the dimension of the holes in the high frequency attenuation section of the through passages.

17. The air blower of claim 13, wherein at least one of the low frequency and high frequency attenuation sections in each of the inlet and outlet mufflers is fitted with a noise absorbent material.

18. The air blower of claim 13, wherein at least one of the low frequency and high frequency attenuation sections in each of the inlet and outlet mufflers is a Helmholtz chamber.

19. The air blower of claim 13, wherein the outlet muffler further has an outlet extension adapted to be connected to one end of an air hose whose other end is connectable to a convective blanket so that the convective blanket may be inflated by the air flow output from the outlet muffler.

20. The air blower of claim 19, wherein the air hose has at least one sensor at its other end and the outlet extension has at least an other sensor, further comprising a circuit that utilizes values of the one and other sensors with reference values to establish a set of stepped values that correspond to each type of different types of air hoses adapted to be coupled to the outlet extension, wherein when a given air hose is coupled to the outlet extension, the circuit effects the motor to rotate the impeller at a rate in accordance to a step value that corresponds to the type of air hose said given air hose is.

* * * * *